United States Patent [19]
Friedman et al.

[11] Patent Number: 5,209,659
[45] Date of Patent: May 11, 1993

[54] METHOD FOR INSTALLING A DENTAL IMPLANT

[75] Inventors: Kurt E. Friedman, Plantation; James E. Davis, Ft. Lauderdale; Bruce L. Nickerson; Richard A. Smolowitz, both of Davie, all of Fla.

[73] Assignee: Impla-Med Incorporated, Sunrise, Fla.

[21] Appl. No.: 718,348

[22] Filed: Jun. 19, 1991

Related U.S. Application Data

[63] Continuation-in-part of Ser. No. 577,789, Sep. 5, 1990, Pat. No. 5,100,323.

[51] Int. Cl.$^5$ ................................................ A61C 8/00
[52] U.S. Cl. ...................................... 433/173; 433/174
[58] Field of Search ............................... 433/174, 173

[56] References Cited

U.S. PATENT DOCUMENTS

| | | | |
|---|---|---|---|
| 3,579,831 | 5/1971 | Stevens | 433/174 |
| 4,599,085 | 7/1986 | Riess et al. | 433/173 |
| 4,713,004 | 12/1987 | Linkow et al. | 433/174 |
| 4,826,434 | 5/1989 | Krueger | 433/174 |
| 4,863,383 | 9/1989 | Grafelmann | 433/174 |
| 4,934,935 | 6/1990 | Edwards | 433/174 |
| 5,061,181 | 10/1991 | Niznick | 433/174 |

OTHER PUBLICATIONS

Brochure from Core-Vent Corporation regarding "Micro-vent Hydroxylapatite Coated Implants".

Primary Examiner—John J. Wilson
Attorney, Agent, or Firm—David P. Gordon

[57] ABSTRACT

Dental implants for supporting and positioning artificial teeth or prosthetic devices are provided. The dental implant is adapted to be installed and ultimately oseointegrated into a predrilled osteotomy site of either the maxilla or mandible. The dental implant has a generally cylindrical body with an apical threaded portion which is screwed and secured into the bone. The cylindrical body also includes an internal threaded bore extending from the second end into the cylindrical body along the longitudinal axis of the cylindrical body. An integral hexagonal shaped protrusion, when viewed along the bore of the cylinder, is preferably provided and extends from the end of the implant proximal the gingiva of the patient. The internal bore of the cylinder extends concentrically through both the annular base and the hexagonal protrusion. The hexagonal protrusion will mate with as corresponding shaped female recess in an abutment which supports and positions artificial teeth or other prosthetic devices above the gingiva or alveolar mucosa which is located above the bone. The abutment rests on both the annular base and the hexagonal projection This mating relation prevents the abutment from rotating around hexagonal projection and thereby maintains the orientation of the abutment and corresponding artificial teeth or prosthetic devices within the mouth.

4 Claims, 3 Drawing Sheets

METHOD FOR INSTALLING A DENTAL IMPLANT

This is a continuation-in-part of Ser. No. 05/577,787 filed on Sep. 5, 1990, now issued as U.S. Pat. No. 5,100,323, which is hereby incorporated by reference herein in its entirety.

BACKGROUND OF THE INVENTION

1. Field of the Invention

This invention relates generally to dental implants. More particularly, this invention relates to endosseous dental implants having external or internal locking means for engaging an artificial dental appliance a dental restoration or prosthesis.

2. Description of Prior Art

There are basically three different types of endosseous implants blades, screws, and cylinders. Blade, screw and cylinder implants all require that a hole or slot first be made in the maxillary or mandibular jawbone prior to the implant being inserted In the case of a screw-type implant, a threaded hole is either tapped in the bone to accept the threaded screw implant, or alternatively a self-tapping threaded implant is screwed directly into the prepared bone. The tops of both these screw-type implants are typically provided with either a hexagonal male projection or an internal female hexagonal arrangement which is adapted to mate with a correspondingly shaped engaging male or female mating surface in a screw driving tool which is used to actually insert the implant into the bone. Following insertion of the screw type implant, the male projection or the female aperture of the implant can be utilized to matingly engage a corresponding female aperture or male projection in a prosthetic component to firmly seat the component and prevent rotation of the prosthetic component with respect to the implant. In this way, the prosthetic component is secured into position with the above screw type implant. A representative example of a screw-type implant is disclosed in U.S. Pat. No. 4,713,004 to Linkow et. al. which discloses an implant having inner and outer screw threads along its elongate body portion and a hexagonal projection at its upper end which is adapted to be engaged for rotation with a wrench type tool.

The prior art cylinder-type implants differ from the screw-type implants in several respects. First, the cylinder-type implants do not have external threads. Second, the cylinder-type implants typically have an open internal threaded central bore extending partially into the implant for the purpose of securing a prosthetic component. Third, the cylinder-type implants are not provided with hexagonal members extending from the tops thereof, because a threading tool is not necessary to install the cylinder-type implant as with a screw implant. In implanting a cylinder-type implant, an unthreaded hole is drilled into the bone, with the inner diameter of the hole being equal to or slightly less than the outer diameter of the cylinder to be installed. The cylinder is then carried to the surgical site by utilizing a carrying post which is threaded into the internal threaded central bore and which projects therefrom. The cylinder implant, with the carrying post extending therefrom, is then press fit into the hole and is gently tapped into place by tapping the carrying post with a small mallet (thereby protecting the implant itself). In the ideal case, a snug, tight fit is provided between the cylinder and the surgical osteotomy hole The choice of whether to use a screw-type or a cylinder-type implant is strictly up to the dental surgeon and has previously been substantially dependent upon the quality, quantity, and geometry of bone underlying the gingiva at the implant site. The cylinder-type implant is often preferred where the bone of the mandible or maxilla is soft or less dense. Since the bone of the maxilla is typically softer than bone matter of the mandible, cylinders are often the implants of choice when used in the maxilla.

As aforementioned, the cylinder implant is installed by pushing the body portion thereof directly into the surgical site drilled into the bone. The top of the cylinder implant is located at approximately the surface of the bone and includes an internal threaded bore extending, into the cylinder body as noted above. This internal threaded bore receives anchoring fasteners such as screws to hold a prosthetic component or restoration in place above the cylinder implant An abutment, which can take many forms and shapes is then placed on top of the cylinder or screw type implant. The abutment serves as a core to provide for retention and/or stability of a replacement tooth or dental prosthesis. The abutment is typically colineal with the central internal threaded bore of the cylinder when the abutment is in place on top of the cylinder. The replacement tooth or prosthesis typically also has an aperture colineal with the bore of the cylinder and the abutment. In such situations, a screw extending through the prosthetic device and the abutment is used to secure the abutment and the prosthetic device to the implant. In other cases, the prosthetic restorations are cemented onto the abutment core.

Heretofore, where the bone closest the gum of the patient is soft, the surgeon utilizing the cylinder-type implant has not had the benefit of any screw-implant engagement with the bone of the patient. Moreover, prior to the teachings of the parent application hereto, the surgeon has not had the advantage of a shaped projection member, mating with a corresponding aperture in the abutment in order to obtain a secure and relatively permanent fit and orientation between the cylinder and the dental replacement structure.

SUMMARY OF THE INVENTION

It is therefore an object of this invention to provide a hybrid implant that combines the advantages of a cylinder implant and the advantages of the screw-type implant.

It is another object of the invention to provide a hybrid implant which is constructed to utilize the wide variety of prosthetic devices already readily available with screw implants.

Another object of this invention is to provide a dental implant which is rigidly securable within the socket or alveolar of a recently extracted tooth or prepared opening to provide a suitable foundation for a prosthesis such as a crown or replacement tooth.

A further object of this invention is to provide a dental implant which does not threadably engage the socket or the open alveolar space of the extracted tooth or other opening in the region underlying the gingiva, but rather is inserted in this region by press fit or tapping impact.

Yet another object of the invention is to provide a dental implant which threadably engages the hard bone which is at approximately the apical third of the implant body, but which does not threadably engage softer bone near the gingiva or alveolar mucosa of the patient, and which further includes an integral male projection member adapted to mate with a corresponding recess disposed within a dental prosthesis in order to resist rotation of the dental prosthesis relative to the dental implant.

In accord with the objects of the invention, an endosseous implant (also referred to as the "hybrid" implant) comprising a rigid cylindrically shaped body having a threaded apical portion is provided. The cylindrical body and threaded apical portion are preferably comprised of commercially pure titanium and are adapted to be initially inserted into the bone of a patient as a conventional cylinder-type implant followed by a screwing (i.e. self-tapping) of the apical portion of the implant into the bone. The cylinder portion of the hybrid implant matches the standard cylinder-type implant, and preferably further includes an upper projection member that accepts the variety of prosthetic components heretofore used only with screw-type implants. The implant body may also include one or more recesses extending into or through the implant body to enhance the osseointegration of the cylinder body with, and the ultimate retention of the cylinder in the surrounding bone.

The cylindrical body portion and, in some cases, the threaded apical portion of the implant are preferably first coated with a titanium plasma spray, and then with hydroxylapatite, to increase the surface area of the implant body and improve the biologic integration of the implant and the bone. Although the combination of hydroxylapatite and the titanium plasma is the preferred coating technique, other coating techniques using these materials, either individually or in combination, as well as other materials that enhance the biological osseointegration process may be used.

A better understanding of the improved dental implant of the invention, and additional objects and advantages of the invention will become apparent to those skilled in the art upon reference to the detailed description and the accompanying drawings.

DETAILED DESCRIPTION OF INVENTION

Figure 1:
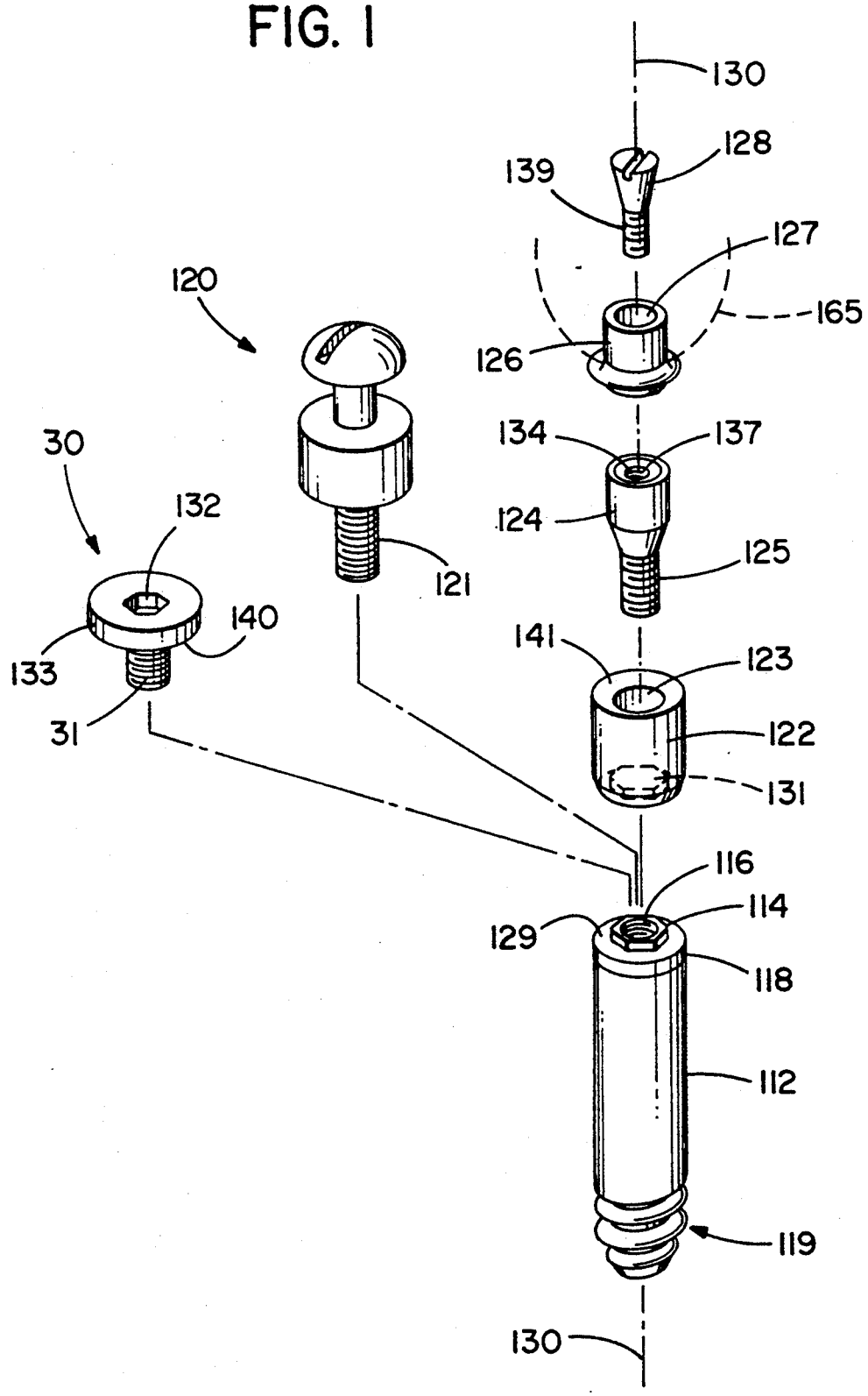
FIG. 1 is an exploded view in perspective the preferred implant of the present invention and various associated components.

With reference to the figures, a dental implant 100 is shown having a cylindrical body portion 112, an outwardly threaded apical portion 119 integral and below the cylindrical body portion 112, and a locking projection 114 integral and above the cylindrical body portion 112. The outwardly threaded apical (bottom end) portion or element 119, has sharp external cutting threads 111 which do not extend beyond the envelope 195 of the cylindrical portion 112; i.e. the outer diameter of threads 111 does not exceed the diameter, "D", of the cylindrical portion 112 cutting threads (although different numbers of threads can be used), and is typically, although not necessarily, from about 1/5 to ⅓ the length of body 112. The threaded portion 119 preferably does not exceed one-half the length of body 112. A typical thread pitch might be about 0.04 inches, while the inner diameter of the threads might be about 3/5 the width of the outer diameter of the threads. Of course, the number, pitch, and inner and outer diameter of the threads can vary widely as desired, as can the ratio of the length of the threaded portion to the total length of the implant.

Figure 2:
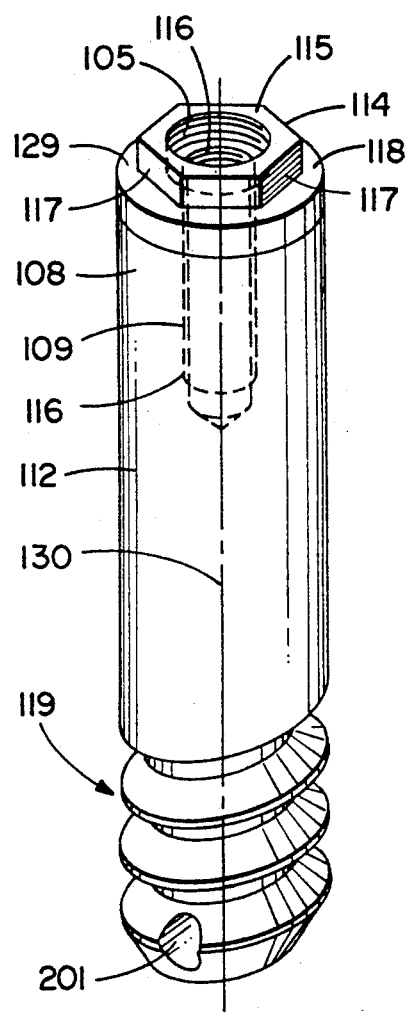
FIG. 2 is a perspective view of the preferred implant of the present invention having a male projection integrally connected to the top of the cylinder body.
Figure 3:
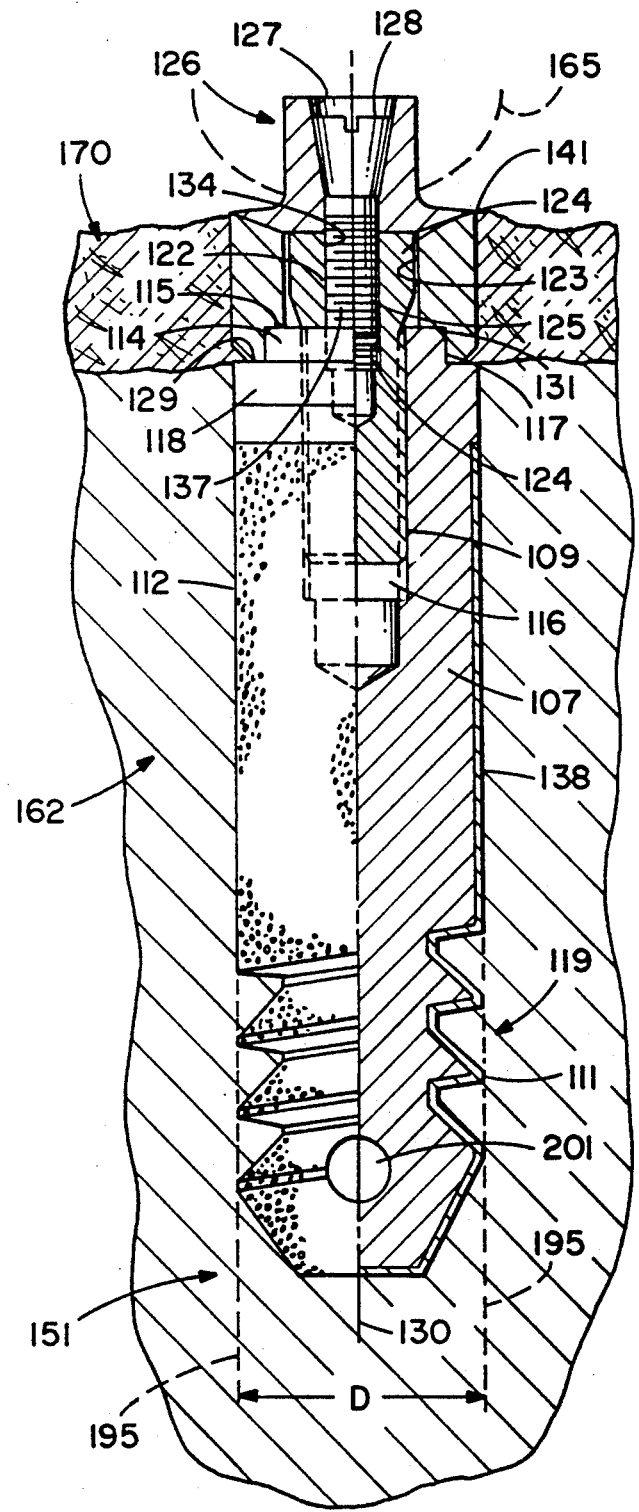
FIG. 3 is an elevation view, partly in section, of the preferred implant of the invention installed in the bone of the maxilla or mandible.
Figure 3A:
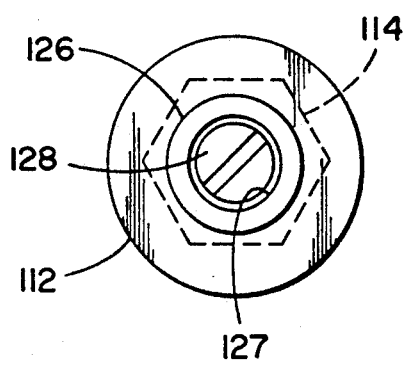
FIG. 3(A) is a plan view of the embodiment of FIG. 3.
Figure 4:
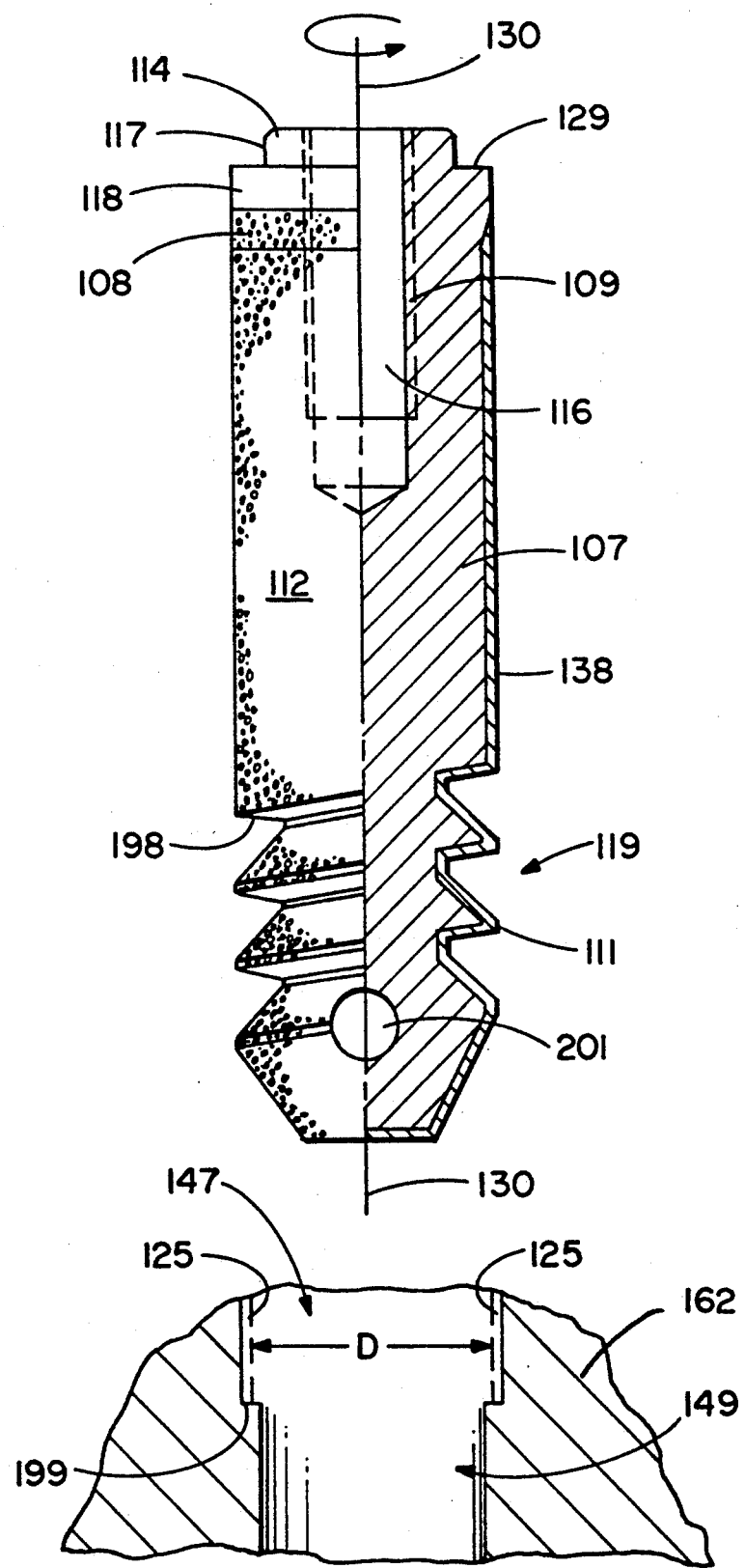
FIG. 4 is an elevation view of the implant of FIG. 3 prior to installation.

As seen in FIGS. 2, 3, and 4, the threaded portion 119 of the dental implant 100 also includes an anchor bore or hole 201 which extends through the implant in a direction perpendicular to the long axis of the implant. The hole 201 is provided to permit bone to grow therein (i.e. ossointegration) which enhances the anchoring of the implant in the bone. Those skilled in the art Will appreciate that the hole 201 may not be required. Moreover, it will be appreciated that the location of the role Could be changed; e.g. such that it is located in the cylindrical body 112 of the implant 100.

The cylindrical body 112 is shown having a concentric annular polished collar or base 118 integrally attached at the upper end 108 of body 112. Extending through the annular collar 118 in a concentric fashion and into the cylindrical body 112 is a threaded central bore 116. Annular collar 118 has a planar top surface 129 at the end of cylindrical portion 112 opposite the threaded portion 119 of body 112. The diameter of body 112 and coextensive annular base 118 typically ranges from 2.0-6.0 millimeters, while the length of body 112, including threaded portion 119, typically ranges from about 5-20 millimeters. Other diameter and length combinations may be utilized.

Affixed to the planar top surface 129 of collar 118 and integral therewith is the projection 114 which has a hexagonal cross-section and a threaded central circular passage 105 (FIG. 2) concentrically surrounding threaded central bore 116. Threaded bore 116 extends only part way down through body 112, e.g. ⅓ to ½, and has internal threads 109, which continue upward through the integral annular collar 118 and projection 114. The sides 117 of hexagonal projection 114, when viewed along the axis 130 of the threaded bore 116, extend downward from the top surface 115 of projection 114 to the top surface 129 of annular collar 118 in a generally perpendicular direction to both top surfaces 115 and 129 and provide engageable surfaces.

A generally cylindrically-shaped abutment member 122 is also provided in conjunction with implant 100. Extending through abutment member 122 is an unthreaded central bore 123 which in axial alignment with the longitudinal axis 130 of threaded bore 116 in cylindrical body 112. Abutment member 122 also has a recess 131 of hexagonal cross-section at its lower end which is concentric with its central bore 123. Recess 131 corresponds in shape and size to the projection 114 to enable a close mating fit therewith. Recess 131 is preferably slightly larger in size than bore 123. With recess 131 of abutment 122 seated on collar 118 and in mating contact with projection 114, abutment 122 may be securely engaged with cylindrical body 112 as hereinafter described. In this engaged position, threaded bore 116 of body 112 and unthreaded bore 123 through abutment 122 are concentric and coaxial with longitudinal axis 130.

When the hexagonal cross-section projection 114 and correspondingly shaped recess 131 are engaged, abutment 122 is prevented from rotating with respect to body 112. Other mating configurations besides the hexagonal configuration shown can be used, provided that rotation of either element causes corresponding rotation of the other elements. Examples of such suitable shapes for the projection and recess are square, rectangle, star, triangle, oval and free formed.

In order to securely engage cylindrical body 112 with abutment 122, an abutment screw 124 with external threads 125 is provided The external threads 125 threadably engage with and correspond to internal threads 109 of bore 116, and abutment screw extends through the non-threaded bore 123 of abutment 122 to engage the internal threads 109 of bore 116 in body 112. An internally threaded bore 134, with threads 137, extends into the upper portion of abutment screw 124. The threaded bore 134 permits the engagement of a prosthetic device 165 which is coupled to a gold cylinder 126 to the abutment 122 (and hence to the cylinder 112) by engaging the external threads 139 of screw 128 Which extends through the gold cylinder 126.

The dental implant 100 (including cylindrical portion 112, projection 114, collar 118, and threaded section 119), and the abutment 112 and abutment screw 124 are all preferably made of commercially pure titanium. Additionally, as hereinbefore noted, the cylindrical body portion 112 and the threaded portion 114 of the implant 100 at their outer surfaces are sometimes provided with a thin coating 138 of hydroxylapatite, titanium plasma, or other materials which aid in the bio-integration of the body 112 with the surrounding bone 162.

In use, an artificial tooth or other prosthetic device 165 is placed around the gold cylinder 126 which has a non-threaded bore 127. A gold screw 128, with external threads 139, is extended through the non-threaded bore 127 of gold cylinder 126, to threadably engage the threaded bore 134 of abutment screw 124 and to securely hold gold cylinder 126 and the prosthetic device 165 fixedly in place relative to the upper surface 141 of abutment 122. Abutment 122 is fixedly engaged to the implant 100, and is therefore also fixed in position to bone 162 to which the implant 100 is engaged as hereinafter described. As so arranged, rotation of prosthetic device 165 about axis 130 of implant 100 is prevented by the engagement of the hexagonal projection 114 of the implant 100 with the hexagonal recess 131 in abutment 122.

In implanting the implant device 100 in a bone 162, a hole which is the same as or slightly smaller in diameter than the diameter of the cylindrical portion 121 of cylindrical section 112 is drilled into the bone 162 to establish an unthreaded bore 147 in bone 162. In addition, an unthreaded concentric bore 149, of slightly smaller diameter than bore 147, is pre-drilled deeper into bone 162. With a temporary installation piece 120 (FIG. 1) with external threads 121 threaded into bore 116 of body 112, the implant device 100 is brought to the surgical sight. The temporary installation piece 120 provides a cap or protective covering for the projection 114 and the threaded bore 116 of the implant. The implant, with its temporary installation cap 120 in place, is inserted in the pre-drilled bore hole 147 in bone 162, for example by gentle tapping with a small mallet on temporary installation cap 120, until the bottom of the threaded portion 119 of the cylindrical section 112 is in a position adjacently above the smaller diameter bore 149. The implant 100 is then screwed into bore 149 of bone 162 via use of a wrench or other tool (not shown) Which matingly engages the installation cap. As the implant 100 is turned about axis 130 the sharp cutting threads 111 of the threaded portion 119 tap into the bone surrounding the narrower bore 149. Eventually, the bottom 198 of the non-threaded portion of the cylindrical section 112 will seat on a shelf 199 which is formed by the junction of the larger diameter bore 147 and the smaller diameter bore 149. The result of utilizing the hybrid implant invention which combines a primarily cylindrical portion 112 with an apical screw portion 119 is a sound threaded engagement of the implant with the harder bone at location 151 apical the prosthesis 165 and the patient's gingiva or alveolar mucosa, and a secure frictional, laterally supporting engagement of the cylindrical portion 112 with the less dense bone closest to the gingiva or alveolar mucosa.

With the implant 100 in place, the temporary installation cap 120 is removed. A cover screw 130 (FIG. 1) having external threads 131, a hexagonal recess 132 opposite threads 131, and a cover member 133 with a planar lower surface 140, is then threaded into bore 116 until the lower surface 140 of the cover member 133 contacts the upper surface 129 of collar 118, thus providing a temporary seal between cover member 133 and the top of bore 116 at the surface of projection 114. Hexagonal recess 132 in cover screw 130 allows a hexagonal tool, i.e. a wrench, to be inserted therein to advance cover screw 130 in into bore 116. Alternately, hexagonal recess 132 may be replaced by a slot running across the top surface of body 133 allowing cover screw 130 to be advanced by the insertion and rotation of a blade-type tool. After the cover member 133 of cover screw 130 has sealingly contacted projection 114, the implant is left in the bone for a period sufficient to permit bio-integration to take place, thereby securing the implant in the bone 162.

After the lapse of a sufficient amount of time to enable bio-integration, cover screw 130 is removed from cylinder 112 by reverse rotation and unthreading to expose bore 116. At this time recess 131 of abutment 122 is placed in a rotationally fixed mating engagement with projection 114. Abutment 122 provides the base support for the subsequent attachment of gold cylinder 126 and a prosthetic device 165, above the gingiva or alveolar mucosa 170 which is above the bone in which the implant 100 is implanted.

As hereinbefore described, abutment screw 124 is placed through the non-threaded bore 123 of abutment 122 so that threads 125 of the abutment screw 124 engage the threads of bore 116. As abutment screw 124 advances into bore 116, the recess 131 of abutment 122 securely engages the projection 114 which is integral with body 112.

Gold cylinder 126, with its attached prosthetic device 165, is then seated on the top of the abutment screw 124 with its bottom portion in contact with abutment screw 124 and its frustoconical surface portion 147 in contact with the similarly shaped surface 141 of abutment 122. Gold screw 128 is inserted through non-threaded bore 127 of gold cylinder 126 and is securely threaded into the threaded bore 134 of abutment screw 124. Gold screw 128 frictionally holds gold cylinder 126, and therefore the corresponding artificial tooth or prosthetic device 165, firmly in place on the top of abutment 122 and abutment screw 124.

Abutment screw 124 is prevented from rotating by its frictional bearing contact with abutment 122, which is in turn prevented from rotating by the interaction of the close mating engagement of projection 114 and recess 131. Since rotation of abutment 122 and abutment screw 124 is prevented, rotation of gold cylinder 126 is also prevented by the frictional bearing engagement of gold cylinder 126 with abutment 122 and abutment screw 124. In this way, the artificial tooth or other prosthetic device 165 attached to gold cylinder 126 is prevented from rotating around body 112 by a simple and effective arrangement which has not heretofore been available in the prior art. Also, the self-tapped threaded engagement of the apical portion of implant 100 with hard dense bone at a location remote from the gingiva or alveolar musoca, together with tight lateral support of the unthreaded cylindrical portion 112 by bone closer to the gingiva or alveolar mucosa, provides enhanced protection against movement of the implant.

There has been described and illustrated herein a dental implant in accordance with the present invention. While particular embodiments of the invention have been described, it is not intended that the invention be limited exactly thereto, as it is intended that the invention be as broad in scope as the art will allow. Thus, while the preferred implant was described as having particular numbers of threads at a given pitch, and being of particular size, etc., those skilled in the art will appreciate that the threaded portion of the hybrid implant can take numerous forms, and hybrid implants can be prepared regardless of size. Further, while the preferred dental implant described and shown includes a hexagonal projection as taught by the parent application hereto, the invention is intended to encompass all implants having a cylindrical top portion and a threaded apical portion, regardless of whether a hexagonal projection is included or not. Thus, for example, the top portion of the implant might have a differently arranged projection extending therefrom. Alternatively, the top portion of the implant might have a female mating surface (hexagonal or otherwise) seated therein. All that is required is that there be some means available which permits the screwing of the hybrid implant into the osteotomy site in the bone, and some means for attaching the prosthesis to the hybrid implant. In a similar vein, it will be appreciated that while a particular abutment was described for permitting connection of the prosthesis to the implant, other abutments can be utilized which screw retained or cemented crowns to the implant. Also, while the method of inserting the hybrid implant into the osteotomy site suggested a certain order of steps, it will be appreciated by those skilled in the art that depending upon the particular arrangement of the hybrid implant, the annular abutment, and the tools used to screw the hybrid implant into the osteotomy site, different steps and/or a different order of steps could be utilized. For example, instead of removing the protective cap after screwing in the hybrid implant, the protective cap could be removed before, depending on the tool used for screwing in the hybrid implant, the arrangement of the top surface of the hybrid implant itself, as well as, in certain circumstances, the preparation of the site. It will therefore be appreciated that yet additional changes and modifications can be made to the invention as described without deviating from the spirit and scope of the invention as so claimed.

I claim:

1. A method of inserting a dental implant into a pre-drilled osteotomy site in a maxilla or mandible bone of a patient, said pre-drilled osteotomy site having a first wider portion proximal the gingiva or alveolar mucosa of the patient and a second coaxial narrower portion apical the gingiva or alveolar mucosa of the patient, said dental implant having an integral body having an extended generally cylindrical portion of a first diameter, and an apical portion having sharp cutting threads on the outer surface thereof, said threads having an outer diameter not exceeding said first diameter of said extended cylindrical portion, said integral body further including a threaded central bore extending from a first end of and at least partially through said cylindrical portion toward said apical portion, said dental implant having a protective cap means screwed into said threaded central bore of said dental implant, said method comprising:

(a) placing said implant, apical portion first into engagement with said first wider portion of said pre-drilled osteotomy site;

(b) tapping and/or pushing said protective cap means to force said dental implant into said pre-drilled osteotomy site until said apical portion of said dental implant reaches said second coaxial narrower portion of said pre-drilled osteotomy site; and (c) gripping and turning said protective cap means while placing pressure on said protective cap means, thereby screwing said apical portion of said dental implant into said narrower portion of said pre-drilled osteotomy site until said extended generally cylindrical portion reaches said narrower portion of said predrilled osteotomy site.

2. A method of inserting a dental implant into a pre-drilled osteotomy site in a maxilla or mandible bone according to claim 1, wherein:
   said step of gripping and turning said protective cap means comprises using a tool to impart rotational and axial force to said protective cap means and hence to said dental implant.

3. A method of inserting a dental implant into a pre-drilled osteotomy site in a maxilla or mandible bone according to claim 1, wherein:
   said step of tapping and/or pushing comprises imparting force to said dental implant in a non-rotational manner.

4. A method of inserting into a maxilla or mandible bone of a patient a dental implant, and providing said patient with a prosthetic device, said dental implant having an integral body having an extended generally cylindrical portion of a first diameter, an apical portion having sharp cutting threads on the outer surface thereof, and a protrusion of hexagonal cross-section and of smaller outer diameter than said first diameter attached to said cylindrical portion and extending away from said apical portion, said sharp cutting threads having an outer diameter not exceeding said first diameter of said extended cylindrical portion, said integral body further including a threaded central bore extending from a first end of and at least partially through said cylindrical portion toward said apical portion, said dental implant having screwed into its threaded central bore a protective cap means during dental implant insertion, said method comprising:

(a) drilling said bone to create an osteotomy site having a first wider portion proximal the gingiva or alveolar mucosa of the patient and a second coaxial narrower portion apical the gingiva or alveolar mucosa of the patient;

(b) placing said implant, apical portion first into engagement with said first wider portion of said pre-drilled osteotomy site;
(c) tapping and/or pushing said protective cap means so as to force said dental implant into said pre-drilled osteotomy site until said apical portion reaches said second coaxial narrower portion of said pre-drilled osteotomy site;
(d) using a tool to grip said protective cap means, and turning said protective cap means while placing pressure on said protective cap means so as to screw said apical portion of said dental implant into said narrower portion of said pre-drilled osteotomy site until said extended generally cylindrical portion reaches said narrower portion of said pre-drilled osteotomy site;
(e) attaching an annular abutment to said dental implant, said annular abutment having a first end for supporting said prosthetic device and a second end having a hexagonal recess corresponding to said protrusion such that when said protrusion is in contact with said recess, said annular abutment is prevented from rotating around said central bore of said dental implant; and
(f) attaching said prosthetic device to said annular abutment.

* * * * *